United States Patent
Panzenbeck (10) Patent No.: US 11,883,232 B2
(45) Date of Patent: Jan. 30, 2024

(54) RADIAL ULTRASOUND CAPSULE AND SYSTEM

(71) Applicant: OLYMPUS MEDICAL SYSTEMS CORPORATION, Hachioji (JP)

(72) Inventor: Jason T. Panzenbeck, Seattle, WA (US)

(73) Assignee: Olympus Medical Systems Corporation, Tokyo (JP)

(*) Notice: Subject to any disclaimer, the term of this patent is extended or adjusted under 35 U.S.C. 154(b) by 783 days.

(21) Appl. No.: 16/127,620

(22) Filed: Sep. 11, 2018

(65) Prior Publication Data
US 2020/0077975 A1    Mar. 12, 2020

(51) Int. Cl.
*A61B 8/12* (2006.01)
*A61B 8/00* (2006.01)
*G01S 15/89* (2006.01)

(52) U.S. Cl.
CPC .............. *A61B 8/12* (2013.01); *A61B 8/4281* (2013.01); *A61B 8/445* (2013.01); *A61B 8/4461* (2013.01); *A61B 8/461* (2013.01); *A61B 8/54* (2013.01); *G01S 15/894* (2013.01)

(58) Field of Classification Search
CPC ......... A61B 8/54; A61B 8/461; A61B 8/4461; A61B 8/4281; A61B 8/445; A61B 8/12; G01S 15/894
See application file for complete search history.

(56) References Cited

U.S. PATENT DOCUMENTS

| | | | | |
|---|---|---|---|---|
| 4,936,307 A * | 6/1990 | Saito | ...................... | G10K 11/35 600/463 |
| 6,302,875 B1 * | 10/2001 | Makower | ................. | A61B 8/12 604/528 |
| 8,211,021 B2 * | 7/2012 | Ichikawa | ............. | A61B 8/4477 600/443 |
| 9,579,080 B2 * | 2/2017 | Fearnot | .................... | A61B 8/12 |
| 10,314,560 B2 * | 6/2019 | Havel | .................. | A61B 8/0891 |
| 10,588,597 B2 * | 3/2020 | Zhao | ........................ | A61B 8/12 |
| 2002/0198470 A1 * | 12/2002 | Imran | .................... | A61B 5/036 600/587 |
| 2003/0023150 A1 * | 1/2003 | Yokoi | ................ | A61B 1/00032 600/300 |

(Continued)

*Primary Examiner* — Angela M Hoffa
(74) *Attorney, Agent, or Firm* — Schwegman Lundberg & Woessner, P.A.

(57) ABSTRACT

A reusable rotating ultrasound capsule for mounting to a distal end of a catheter. An exemplary device includes a motor compartment having a proximal face and a distal end. A sensor compartment includes a cap that seals with the motor compartment. A motor located within the motor compartment includes a drive component and a shaft rotatably coupled to the drive component and extending distally from the motor compartment into the sensor compartment. The shaft includes an ultrasound transducer. A plurality of electrical contacts are mounted on the proximal face. At least two of the electrical contacts are electrically coupled to the motor. A rotational electrical coupler includes a rotational component mechanically coupled to the shaft and electrically coupled to the ultrasound transducer and a stationary component mechanically coupled to the motor compartment and electrically coupled to one or more of the plurality of electrical contacts.

19 Claims, 6 Drawing Sheets

(56) References Cited

U.S. PATENT DOCUMENTS

| | | | |
|---|---|---|---|
| 2005/0119577 A1* | 6/2005 | Taniguchi | A61B 8/4461 600/459 |
| 2005/0240147 A1* | 10/2005 | Makower | A61B 17/3201 604/96.01 |
| 2007/0067021 A1* | 3/2007 | Haverkost | A61F 2/2418 623/1.24 |
| 2007/0167824 A1* | 7/2007 | Lee | G10K 11/352 600/463 |
| 2009/0270736 A1* | 10/2009 | Miyamoto | A61B 8/12 600/462 |
| 2011/0251458 A1* | 10/2011 | Terliuc | A61B 1/31 600/116 |
| 2014/0187949 A1* | 7/2014 | Zhao | A61B 17/00234 600/443 |
| 2014/0257105 A1* | 9/2014 | Dausch | A61B 8/4281 600/445 |
| 2019/0387961 A1* | 12/2019 | Bansal | A61B 10/04 |

\* cited by examiner

RADIAL ULTRASOUND CAPSULE AND SYSTEM

BACKGROUND

The statements in this section merely provide background information related to the present disclosure and may not constitute prior art.

The tools that are currently available for the ultrasound visualization and sampling of peripheral lung tumors are limited in their range of motion and diagnostic capabilities. Typically, during peripheral sampling a guide sheath is fed through a bronchoscope and extended so far beyond the reach of the bronchoscope that the distal end of the guide sheath is not visible. A radial endobronchial ultrasound (rEBUS) probe is then threaded through the guide sheath and used to determine the approximate location of the tumor.

Current radial ultrasound (US) sensors require a drive cable to rotate the single element for a full 360 degree picture. In a long tortuous path with diameter constraints, rotational correspondence between a handle and the distal US probe becomes difficult. A drive cable also uses up valuable space in a catheter.

SUMMARY

The present invention provides a reusable capsule encompassing a rotating ultrasound sensor for mounting to a distal end of a catheter sized to be used in an endoscope device, such as a bronchoscope.

An exemplary device includes: a housing including: a motor compartment including: a proximal face; and a distal end, wherein the motor compartment has a longitudinal axis; and a cap configured to seal with the motor compartment in order to form a sensor compartment; a motor located within the motor compartment, the motor includes: a drive component; and a shaft rotatably coupled to the drive component and extending distally from the motor compartment into the sensor compartment, the shaft has a longitudinal axis that is parallel to the longitudinal axis of the motor compartment; an ultrasound transducer coupled to the shaft; a plurality of electrical contacts mounted on the proximal face, wherein at least two of the electrical contacts are electrically coupled to the motor; and a rotational electrical coupler including: a rotational component mechanically coupled to the shaft and electrically coupled to the ultrasound transducer; and a stationary component mechanically coupled to the motor compartment and electrically coupled to one or more of the plurality of electrical contacts.

In one aspect of the invention, the proximal face of the motor compartment includes a connection mechanism.

In another aspect of the invention, the motor compartment has a width dimension being perpendicular to the motor compartment longitudinal axis, wherein the width dimension is less than 3 mm or is less than 2 mm.

In still another aspect of the invention, the cap is made of one or more materials that are permeable to an ultrasound signal. The sensor compartment is filled with a fluid configured to transmit an ultrasound signal.

In other aspects of the invention, the cap includes one or more orientation pins, the pins being formed of one or more materials that are non-permeable to an ultrasound signal. The one or more orientation pins comprise at least two pins located on the same half of a cross-sectional dimension of the cap.

In yet other aspects of the invention, a catheter is included. The catheter has a proximal end including an access port; a distal end including: a distal face including a plurality of electrical contacts; and a side exit port located proximal from the distal face; a lumen configured to extend from the access port to the exit port; a ramp located at a distal end of the lumen; and a plurality of electrical connectors accessible from the proximal end of the catheter, wherein the plurality of electrical connectors are connected to at least a portion of the plurality of electrical contacts of the distal face. The diameter of the lumen is at least 50% or 80% of a diameter of the catheter.

In still other aspects of the invention, a system includes a signal processor; a display device in signal communication with the signal processor and a motor controller electrically connected to the motor via the second component. The second component includes: one or more electrical contacts located at a proximal end of the capsule; and a rotational electrical coupler configured to electrically connect the ultrasound transducer to at least one of the electrical contacts.

In further aspects of the invention, a medical device is being slidably received within the lumen.

Further features, advantages, and areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustration purposes only and are not intended to limit the scope of the present disclosure in any way. The components in the figures are not necessarily to scale, emphasis instead being placed upon illustrating the principles of the invention. In the drawings.

DETAILED DESCRIPTION

The following description is merely exemplary in nature and is not intended to limit the present disclosure, application, or uses.

Figure 1:
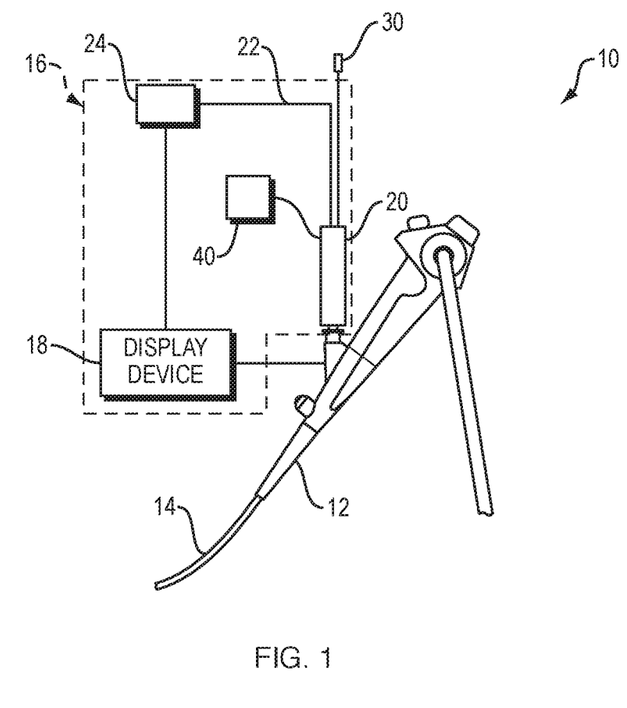
FIG. 1 illustrates an example of a bronchoscope system formed in accordance with an embodiment of the present invention.

Referring now to FIG. 1, a bronchoscope system 10 includes a bronchoscope 12 with an insertion tube 14, a radial ultrasound system 16. The radial ultrasound system 16 includes a signal processor 24, a display device 18, a wire 22 connected to a radial ultrasound capsule (not shown) via a handle device 20. The radial ultrasound system 16 also includes a motor controller 40 connected to a distal motor (not shown) via the handle device 20.

A medical device 30, such as a needle for sampling and/or medicant delivery, is slidably received within a lumen of a catheter (not shown). The catheter is attached at a proximal end to the handle device 20. A radial ultrasound capsule (not shown) is attached to a distal end of the catheter and is electrically connected to the motor controller 40 and the signal processor 24 via the wire 22. The catheter is passed through the handle of the bronchoscope 12 and the insertion tube 14.

The display device 18 is in wired or wireless signal communication with the bronchoscope 12 and/or the signal processor 24. The display device 18 presents images generated based on information received from the bronchoscope 12 and/or the signal processor 24 that receives image information from a radial ultrasound transducer (not shown) of the radial ultrasound probe. A diagnostic bronchoscope (e.g., BF-P190 produced by Olympus®) is an example of the bronchoscope 12.

Figure 2:
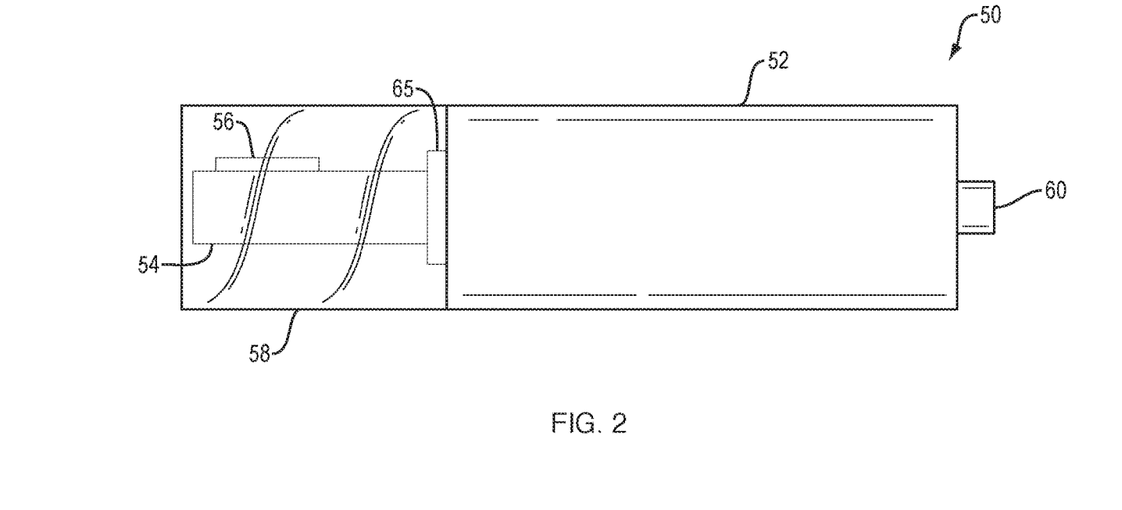
FIG. 2 is a side view of a radial ultrasound capsule formed in accordance with an embodiment of the present invention and used with the system of FIG. 1.

As shown in FIG. 2, a radial ultrasound capsule 50 is a capsule device having a motor 52 and an ultrasound permeable cap 58. The cap 58 is sealed at a distal end of the motor 52 in order to create a sensor cavity. The motor 52 includes a rotating shaft 54 that extends from the distal end of a base of the motor into the sensor cavity. An ultrasound transducer 56 is attached to the shaft 54. An electrical coupling device 65 includes components attached to the shaft 54 and the motor 52 or housing of the motor 52. The cap 58 is made of a material that allows ultrasound signals to pass therethrough. In one embodiment, the sensor cavity is filled with a fluid for allowing ultrasound signals to pass to and through the cap 58.

Figure 3:
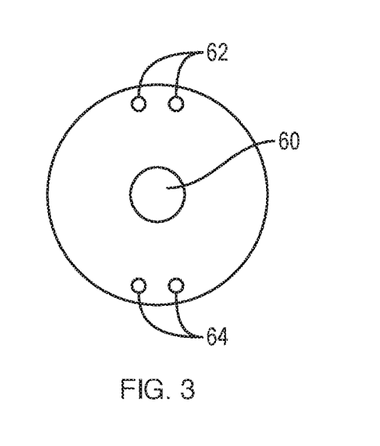
FIG. 3 is a plan view of a proximal end of the capsule of FIG. 2.

As shown in FIG. 3, a proximal face of the capsule 50 includes a plug or knob 60 that protrudes from the proximal face. The plug or knob at 60 allows the capsule 50 to attach to a catheter (see FIG. 4). The diameter of the capsule 50 may be between 0.5 mm to 4 mm. An example of the motor 52 and the shaft 54 is a geared motor or a micromotor, such as that made by Namiki®. The proximal face of the capsule 50 also includes contacts 62 that connect to the motor 52.

Figure 4:
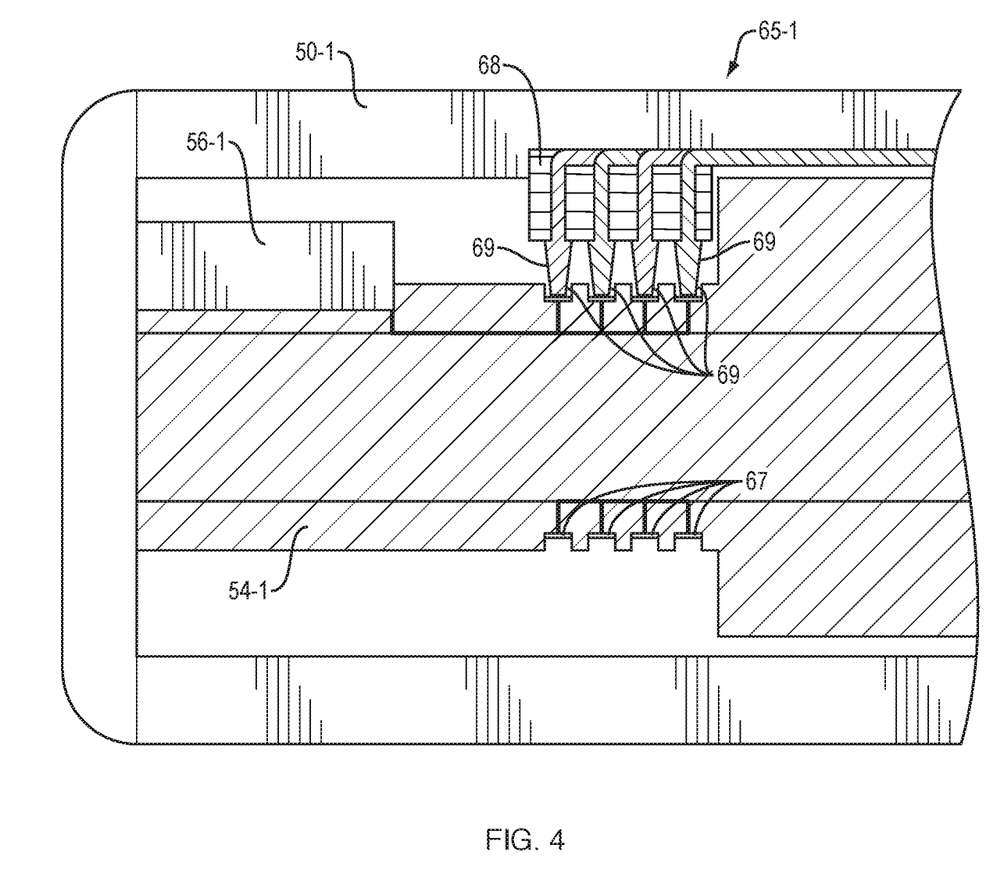
FIG. 4 is cross-sectional view of a portion of a device similar to that shown in FIG. 2.

FIG. 4 shows a cross-sectional view of a distal end of an exemplary capsule with an exemplary electrical coupling device 65-1. The electrical coupling device 65-1 includes one or more ring leads/traces 67 located within annular grooves on a rotating shaft 54-1 similar to the shaft 54 of FIG. 2. The ring leads/traces 67 connect via leads to an ultrasound transducer 56-1 located on the shaft 54-1. The electrical coupling device 65-1 also includes a stationary component 68. The stationary component 68 is mounted to a capsule 50-1 and includes one or more protruding brushes 69 that make electrical contact with the ring leads/traces 67. The one or more brushes 69 connect to one or more electrical contacts located on a proximal face of the capsule 50-1 similar to the capsule 50. Other types of coupling devices may be used.

In one embodiment, the one or more brushes 69 may be electrically connected to one or more motor contacts similar to the motor contacts 62. In this configuration, the signals produced by the transducer 56-1 are modulated before being sent to the motor contacts. The signal processor 24 would include a demodulator if the ultrasound signals were to be sent over the DC power line(s) connected between the motor 52 and the motor controller 40.

Figure 5:
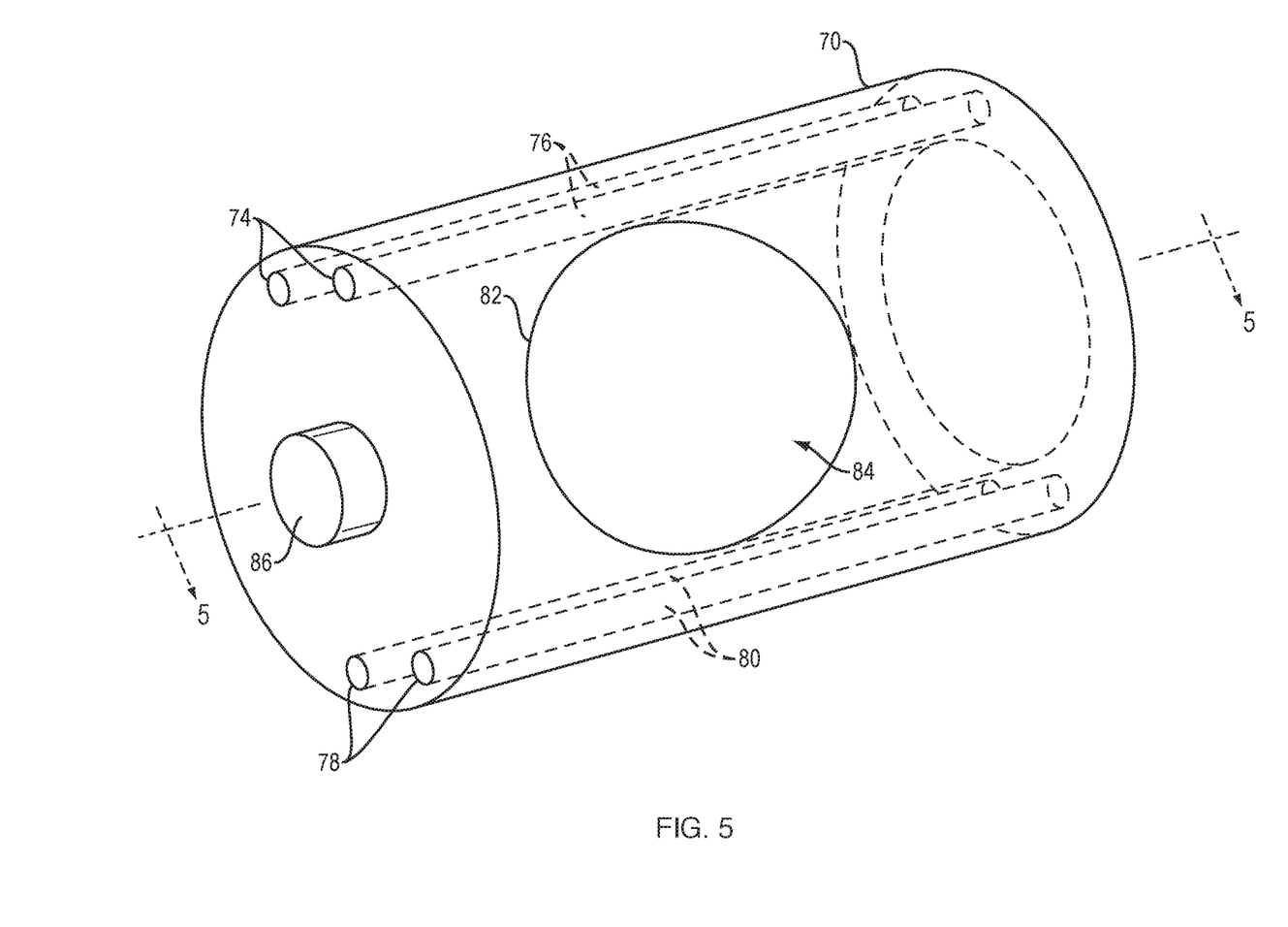
FIG. 5 a perspective view of a distal end of catheter formed in accordance with an embodiment of the present invention and used with the system of FIG. 1.

FIG. 5 is a perspective, x-ray view of a distal end of a catheter 70 that electrically and mechanically couples to the radial ultrasound capsule 50 or 50-1. A distal face of the catheter 70 includes multiple contacts 74, 78 that correspond in position to contacts 62, 64 on the proximal face of the capsule 50. The contacts 74, 78 connect via traces/wires 76, 80 to the signal processor 24 or the motor controller 40. If the ultrasound signal is modulated over the motor power lines as described above, then only one set of contacts and associated traces/wires need to be included in the catheter 70.

The catheter 70 includes a side port 82 located near the distal end. The side port 82 provides access to a lumen 84 that extends all the way to a proximal end of the catheter 70. The lumen 84 is sized to receive the medical device 30. In one embodiment, the diameter of the lumen 84 is between 10 percent and 90 percent of the diameter of the catheter 70.

The distal face of the catheter 70 includes a knob receiving cavity 86 configured to receive the knob 60 of the capsule 50. In one embodiment, the knob 60 and the knob cavity 86 provide a threaded or snap fit connection. Other connection methods may be used.

Figure 6:
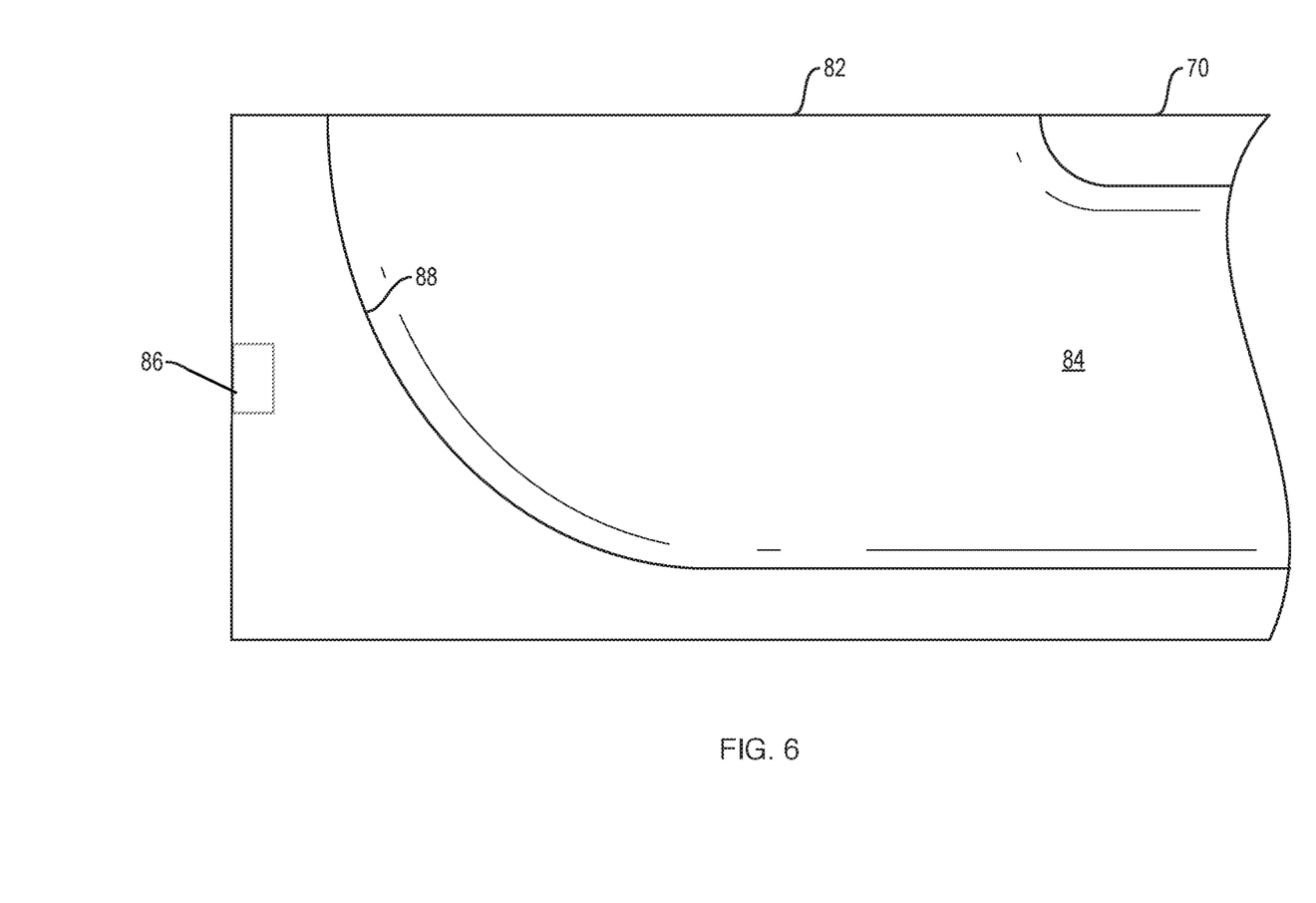
FIG. 6 is a cross-sectional view of a portion of a distal end of the catheter of FIG. 5.

FIG. 6 is a cross-sectional view of the distal end of the catheter 70. The distal end of the lumen 84 includes a ramp 88 configured to allow the medical device 30 to be deflected toward the side port 82.

In one embodiment, the catheter 70 is made of a braided (stainless steel) sheath with PTFE liners in the lumens and Pebax® making up the body and the outer jacket. Other comparable materials may be used. The ramp 88 may be included in a cap section (not shown) that is separate from the catheter 70. The cap section may be made out of polycarbonate, PEEK, Ultem™, TPX® (polymethylpentene) or any biocompatible material that does not reflect ultrasound signals. The cap section would be attachable to the distal end of the catheter 70 and the proximal end of the capsule 50.

Figure 7:
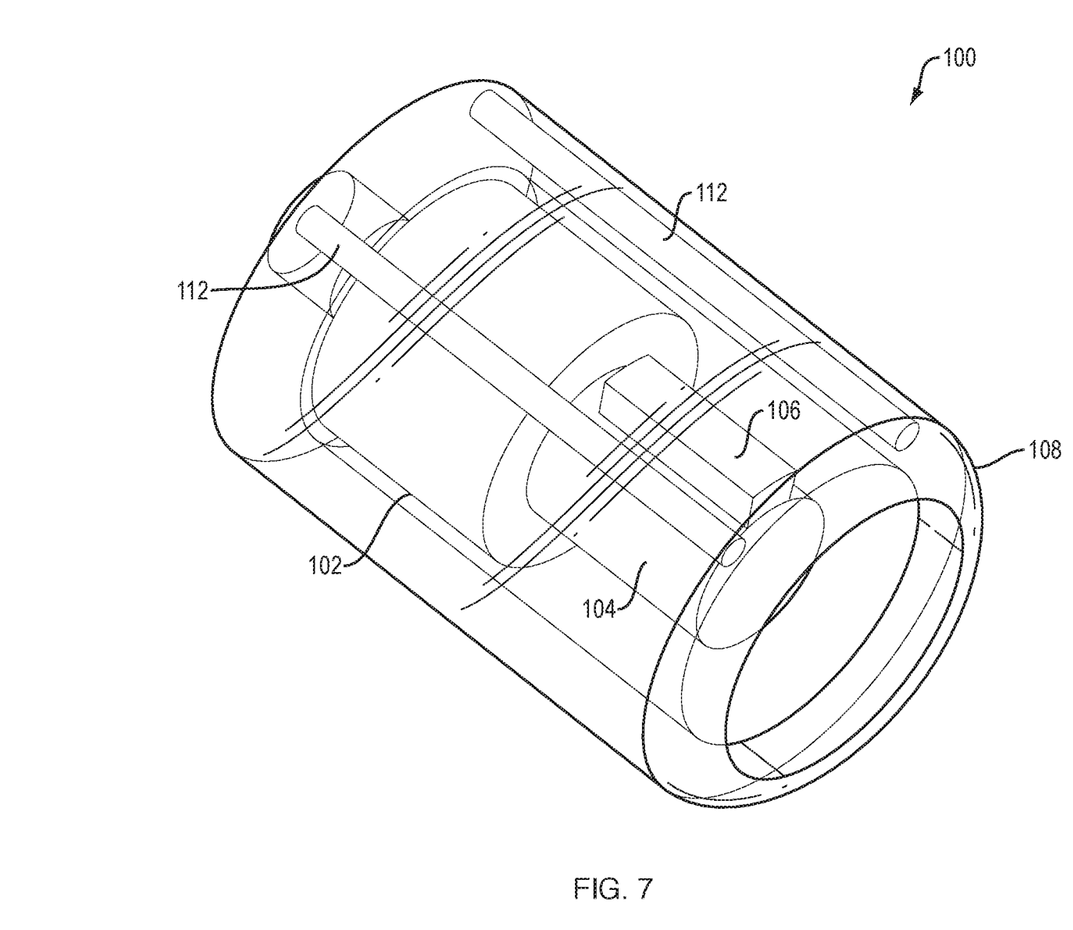
FIG. 7 is a perspective view of a distal end of a radial ultrasound capsule formed in accordance with an embodiment of the present invention and used with the system of FIG. 1.

FIG. 7 illustrates a perspective view of an ultrasound capsule 100. The ultrasound capsule 100 includes one or more ultrasound echogenic orientation pins 112 that are inserted into or formed within a cap 108. The cap 108 houses a motor 102 with a rotating shaft 104. An ultrasound transducer 106 is mounted to the rotating shaft 104. In one embodiment, the orientation pins 112 are located within the same half of the cap 108. The orientation pins 112 extend from a proximal end to a distal end of the cap 108. The orientation pins 112 may extend longitudinally within the cap 108 just in the area where the transducer 108 produces ultrasound signals. In one embodiment, the orientation pins 112 are within 90 degrees of each other along the arc of the cap 108. In one embodiment, the orientation pins 112 are within 45 degrees of each other along the arc of the cap 108. The orientation pins are visible on the ultrasound image and thus alert the user to the rotational orientation of the distal end of the catheter 70 and the medical device 30 relative to a target, such as a tumor or lesion. Not shown are electrical leads and contacts that would be similar to those described in the other embodiments above.

EMBODIMENTS

A. A device comprising: a housing comprising: a motor compartment comprising: a proximal face; and a distal end, wherein the motor compartment has a longitudinal axis; and a cap configured to seal with the motor compartment in order to form a sensor compartment; a motor located within the motor compartment, the motor comprises: a drive component; and a shaft rotatably coupled to the drive component and extending distally from the motor compartment into the sensor compartment, the shaft has a longitudinal axis that is parallel to the longitudinal axis of the motor compartment; an ultrasound transducer coupled to the shaft; a plurality of electrical contacts mounted on the proximal face, wherein at least two of the electrical contacts are electrically coupled to the motor; and a rotational electrical coupler comprising: a rotational component mechanically coupled to the shaft and electrically coupled to the ultrasound transducer; and a stationary component mechanically coupled to the motor compartment and electrically coupled to one or more of the plurality of electrical contacts.

B. The device of A, wherein the proximal face of the motor compartment comprises a connection mechanism.

C. The device of A or B, wherein the motor compartment comprises a width dimension being perpendicular to the motor compartment longitudinal axis, wherein the width dimension is less than 3 mm.

D. The device of A, B or C, wherein the motor compartment comprises a width dimension being perpendicular to the motor compartment longitudinal axis, wherein the width dimension is less than 2 mm.

E. The device of A, B, C or D, wherein the cap comprises one or more materials that are permeable to an ultrasound signal.

F. The device of A, B, C, D or E, wherein the sensor compartment is filled with a fluid configured to transmit an ultrasound signal.

G. The device of A, B, C, D, E or F, wherein the cap comprises one or more orientation pins, the pins being formed of one or more materials that are non-permeable to an ultrasound signal.

H. The device of G, wherein the one or more orientation pins comprise at least two pins located on the same half of a cross-sectional dimension of the cap.

I. A system comprising: an ultrasound capsule comprising: a housing comprising: a motor compartment comprising: a proximal face; and a distal end, wherein the motor compartment has a longitudinal axis; and a cap configured to seal with the motor compartment in order to form a sensor compartment; a motor located within the motor compartment, the motor comprises: a drive component; and a shaft rotatably coupled to the drive component and extending distally from the motor compartment into the sensor compartment, the shaft has a longitudinal axis that is parallel to the longitudinal axis of the motor compartment; an ultrasound transducer coupled to the shaft; a plurality of electrical contacts mounted on the proximal face, wherein at least two of the electrical contacts are electrically coupled to the motor; and a rotational electrical coupler comprising: a rotational component mechanically coupled to the shaft and electrically coupled to the ultrasound transducer; and a stationary component mechanically coupled to the motor compartment and electrically coupled to one or more of the plurality of electrical contacts; and a catheter comprising: a proximal end comprising an access port; a distal end comprising: a distal face comprising a plurality of electrical contacts; and a side exit port located proximal from the distal face; a lumen configured to extend from the access port to the exit port; a ramp located at a distal end of the lumen; and a plurality of electrical connectors accessible from the proximal end of the catheter, wherein the plurality of electrical connectors are connected to at least a portion of the plurality of electrical contacts of the distal face.

J. The system of I, wherein a diameter of the lumen is at least 50% of a diameter of the catheter.

K. The system of I or J, wherein a diameter of the lumen is at least 80% of a diameter of the catheter.

L. The system of I, J or K, wherein the ultrasound capsule comprises a first connection device, wherein the catheter comprises a second connection device, wherein the first and second connection devices allow the ultrasound capsule and the catheter to removable connected to each other.

M. The system of I, J, K or L, wherein the ultrasound capsule and catheter are configured to be received by a working channel of an endoscope.

N. A system comprising: a signal processor; a display device in signal communication with the signal processor; a catheter comprising a lumen; and a capsule comprising: a motor comprising a rotating member; a ultrasound transducer attached to the rotating member of the motor; a first component for mechanically attaching the capsule to the catheter; and a second component for electrically attaching the motor and the ultrasound transducer to the catheter, wherein the catheter comprises a connection component configured to electrically connect the signal processor to the capsule, wherein the signal processor is configured to generate one or more images based on data received from the ultrasound transducer via the second component.

O. The system of N, further comprising a motor controller electrically connected to the motor via the second component.

P. The system of N or O, wherein the second component comprises: one or more electrical contacts located at a proximal end of the capsule; and a rotational electrical coupler configured to electrically connect the ultrasound transducer to at least one of the electrical contacts.

Q. The system of N, O or P, wherein the capsule and catheter are configured to be received by a working channel of an endoscope.

R. The system of N, O, P or Q, wherein the lumen comprises: an access port located near a proximal end of the catheter; and an exit port located near a distal face of the capsule.

S. The system of N, O, P, Q or R, further comprising a medical device being slidably received within the lumen.

The description of the invention is merely exemplary in nature and variations that do not depart from the gist of the invention are intended to be within the scope of the invention. Such variations are not to be regarded as a departure from the spirit and scope of the invention.

What is claimed is:
1. A radial ultrasound device comprising:
   a catheter comprising a proximal end, a distal end, and a lumen extending from the proximal end to a side exit port adjacent the distal end;
   a housing coupled to the distal end of the catheter and having a same diameter as a distal face of the distal end of the catheter, the housing comprising:
     a motor compartment comprising:
       a proximal face mechanically and electrically coupled to a distal face of the distal end of the catheter; and
       a distal end,
       wherein the motor compartment has a longitudinal axis; and
     a cap configured to seal with the motor compartment in order to form a sensor compartment, the cap includes two orientation pins oriented parallel to a longitudinal axis of the cap less than 180° from each other along an arc of the cap;
     a motor located within the motor compartment, the motor comprises:
       a drive component; and a shaft rotatably coupled to the drive component and extending distally from the motor compartment into the sensor compartment;
an ultrasound transducer coupled to the shaft at a longitudinal position collocated with the two orientation pins;
a plurality of electrical contacts mounted on the proximal face, wherein at least two of the electrical contacts are electrically coupled to the motor; and
a rotational electrical coupler comprising:
a rotational component mechanically coupled to the shaft and electrically coupled to the ultrasound transducer; and
a stationary component mechanically coupled to the motor compartment and electrically coupled to one or more of the plurality of electrical contacts.

2. The device of claim 1, wherein the proximal face of the motor compartment comprises a connection mechanism.

3. The device of claim 1, wherein the motor compartment comprises a width dimension being perpendicular to the motor compartment longitudinal axis, wherein the width dimension is less than 3 mm.

4. The device of claim 1, wherein the motor compartment comprises a width dimension being perpendicular to the motor compartment longitudinal axis, wherein the width dimension is less than 2 mm.

5. The device of claim 1, wherein the cap comprises one or more materials that are permeable to an ultrasound signal.

6. The device of claim 5, wherein the sensor compartment is filled with a fluid configured to transmit an ultrasound signal.

7. A radial ultrasound capsule system comprising:
an ultrasound capsule comprising:
a housing comprising:
a motor compartment comprising:
a proximal face; and
a distal end, wherein the motor compartment has a longitudinal axis; and
a cap configured to seal with the motor compartment in order to form a sensor compartment, the cap includes two orientation pins oriented parallel to a longitudinal axis of the cap less than 180° from each other along an arc of the cap;
a motor located within the motor compartment, the motor comprises:
a drive component; and
a shaft rotatably coupled to the drive component and extending distally from the motor compartment into the sensor compartment, the shaft has a longitudinal axis that is parallel to the longitudinal axis of the motor compartment;
an ultrasound transducer coupled to the shaft, wherein the ultrasound transducer is located at the same longitudinal position as the two orientation pins;
a plurality of electrical contacts mounted on the proximal face, wherein at least two of the electrical contacts are electrically coupled to the motor; and
a rotational electrical coupler comprising:
a rotational component mechanically coupled to the shaft and electrically coupled to the ultrasound transducer; and
a stationary component mechanically coupled to the motor compartment and electrically coupled to one or more of the plurality of electrical contacts; and
a catheter comprising:
a proximal end comprising an access port;
a distal end comprising:
a distal face of a same diameter as a proximal face of the ultrasound capsule and coupled to the proximal face of the motor compartment of the housing of the ultrasound capsule and comprising a plurality of electrical contacts; and
a side exit port located proximal from the distal face;
at least one lumen configured to extend from the access port to the exit port;
a ramp located at a distal end of one of the at least one lumen; and
a plurality of electrical connectors accessible from the proximal end of the catheter, wherein the plurality of electrical connectors are connected to at least a portion of the plurality of electrical contacts of the distal face.

8. The system of claim 7, wherein a diameter of the lumen is at least 30% of a diameter of the catheter.

9. The system of claim 7, wherein a diameter of the lumen is at least 80% of a diameter of the catheter.

10. The system of claim 7, wherein the ultrasound capsule comprises a plug extending from the proximal face,
wherein the catheter comprises a recess adapted to receive the plug,
wherein the plug threads or snaps into the recess to allow the ultrasound capsule and the catheter to mechanically and electrically connect to each other.

11. The system of claim 7, wherein the ultrasound capsule and catheter are configured to be received by a working channel of an endoscope.

12. A radial ultrasound capsule system comprising:
a catheter comprising:
a proximal end;
a distal end comprising:
a side exit port located proximal from the distal face;
a lumen configured to extend from the proximal end to the side exit port;
a ramp located at a distal end of the lumen; and
a cap configured to connect to the distal end of the catheter, the cap includes two orientation pins oriented parallel to a longitudinal axis of the cap less than 180° from each other along an arc of the cap, wherein the two orientation pins extend from a proximal end of the cap to a distal end of the cap; and
an ultrasound device sealed within the cap comprising;
a motor;
a rotating shaft coupled to the motor; and
an ultrasound transducer coupled to a distal end of the rotating shaft,
wherein a proximal face of the cap is a same diameter as the distal face of the distal end of the catheter.

13. The system of claim 12, wherein a diameter of one of the lumen is at least 30% of a diameter of the catheter.

14. The system of 12, wherein a diameter of one of the lumen is at least 80% of the diameter of the catheter.

15. The system of claim 12, wherein the catheter is configured to be received by a working channel of an endoscope.

16. The system of claim 12, wherein the cap comprises one of more materials that are permeable to an ultrasound signal.

17. The system of claim 12, wherein the cap includes a sensor compartment filled with a fluid configured to transfer an ultrasound signal.

18. The system of claim 12, wherein the ultrasound device comprises a plug extending from a proximal face of a housing,
   wherein the catheter comprises a recess on the distal end adapted to receive the plug.

19. The system of claim 18, wherein the plug threads or snaps into the recess to mechanically and electrically couple the ultrasound device to the distal end of the catheter.

\* \* \* \* \*

UNITED STATES PATENT AND TRADEMARK OFFICE
CERTIFICATE OF CORRECTION

PATENT NO. : 11,883,232 B2  
APPLICATION NO. : 16/127620  
DATED : January 30, 2024  
INVENTOR(S) : Jason T. Panzenbeck Page 1 of 1

It is certified that error appears in the above-identified patent and that said Letters Patent is hereby corrected as shown below:

In the Claims

In Column 7, Line 32, in Claim 6, delete "transmit" and insert --transfer-- therefor In Column 8, Line 55-56, in Claim 12, delete "comprising;" and insert --comprising:-- therefor In Column 8, Line 66, in Claim 14, delete "12," and insert --claim 12,-- therefor In Column 8, Line 67, in Claim 14, delete "the" and insert --a-- therefor In Column 9, Line 5, in Claim 16, delete "of" and insert --or-- therefor Signed and Sealed this  
Eighteenth Day of March, 2025

Coke Morgan Stewart  
*Acting Director of the United States Patent and Trademark Office*